United States Patent [19]

Varma

[11] 4,257,969
[45] Mar. 24, 1981

[54] 16,17-DIHYDROXYPREGNENE-21-CARBOXYLIC ACIDS AND DERIVATIVES

[75] Inventor: Ravi K. Varma, Belle Mead, N.J.

[73] Assignee: E. R. Squibb & Sons, Inc., Princeton, N.J.

[21] Appl. No.: 114,475

[22] Filed: Jan. 23, 1980

[51] Int. Cl.$^3$ ................................................ C07J 9/00
[52] U.S. Cl. ...................... 260/397.1; 260/239.55 D; 260/397.3; 260/397.45
[58] Field of Search ...................................... 260/397.1

[56] References Cited

U.S. PATENT DOCUMENTS

| | | | |
|---|---|---|---|
| 3,919,421 | 11/1975 | Laurent et al. | 260/239.55 D |
| 3,956,347 | 5/1976 | Laurent et al. | 260/397.1 |
| 4,049,804 | 5/1977 | Laurent et al. | 260/397.1 |

OTHER PUBLICATIONS

Smith et al., "JACS," vol. 82, Sep. 5, 1960, pp. 4625 to 4629.
Laurent et al., Journal of Steroid Biochemistry 6:(1975), pp. 185–192.
Monder et al., "Journal of Steroid Biochemistry," 8:(1977), pp. 897–908.
Obayashi et al., Chem. Pharm. Bull. (6) 27 (1979), pp. 1352–1349.

*Primary Examiner*—Elbert L. Roberts
*Attorney, Agent, or Firm*—Lawrence S. Levinson; Donald J. Barrack

[57] ABSTRACT

Topical antiinflammatory activity is exhibited by 16,17-dihydroxypregnene-21-carboxylic acids and esterified derivatives thereof.

9 Claims, No Drawings

16,17-DIHYDROXYPREGNENE-21-CARBOXYLIC ACIDS AND DERIVATIVES

BRIEF DESCRIPTION OF THE INVENTION

Steroids having the formula

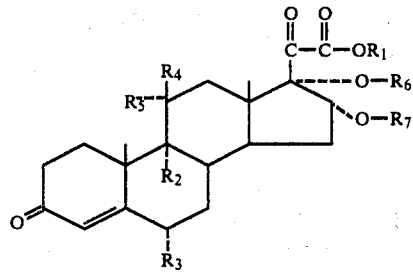

and the 1,2-dehydro derivatives thereof, have useful topical antiinflammatory activity. In formula I, and throughout the specification, the symbols are as defined below.

$R_1$ is alkyl of 1 to 10 carbon atoms, aryl, or arylalkyl;
$R_2$ is hydrogen or halogen;
$R_3$ is hydrogen, fluorine or methyl;
$R_4$ is chlorine, fluorine, hydroxy or

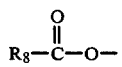

(wherein $R_8$ is alkyl) and $R_5$ is hydrogen, or $R_4$ and $R_5$ together are =O; and
$R_6$ and $R_7$ each is independently hydrogen,

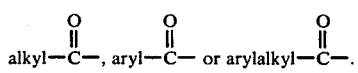

The terms "alkyl" and "alkoxy", as used throughout the specification (unless otherwise defined), refer to both straight and branched chain groups having 1 to 6 carbon atoms.

The term "aryl", as used throughout the specification, refers to phenyl or phenyl substituted with one or more halogen, alkyl and alkoxy groups.

The term "halogen", as used throughout the specification, refers to fluorine, chlorine, bromine and iodine.

DETAILED DESCRIPTION OF THE INVENTION

The steroids of this invention can be prepared from the corresponding $\Delta^{4,16}$-steroidal-21-carboxylic acid esters having the formulas

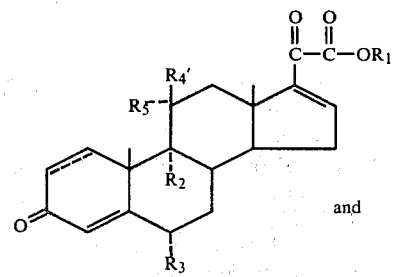

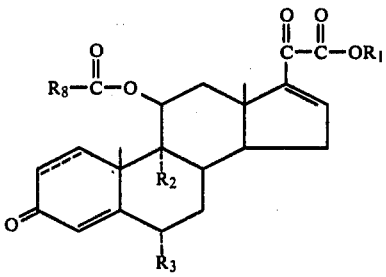

In formulas II and IIa, and throughout the specification, a dotted line in the 1,2-position of a steroid represents the optional presence of ethylenic unsaturation, and $R_4'$ is chlorine, fluorine or hydroxy, or together with $R_5$ is =O. The preparation of a steroid of formula II is disclosed in United States patent application Ser. No. 33,357, filed Apr. 26, 1979.

As disclosed therein, a steroid having the formula

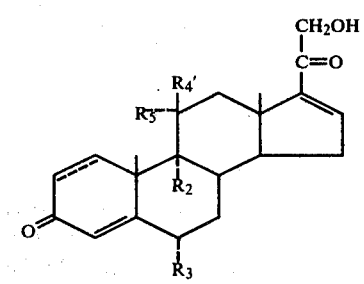

can be oxidized to the corresponding aldehyde having the formula

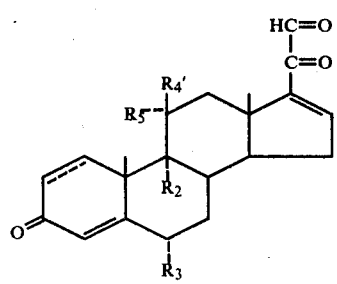

using oxygen (or air) and a catalyst such as copper acetate. The reaction can be run in an alcohol solvent.

If the above described oxidation reaction is carried out in the presence of oxygen (e.g., by bubbling air through the reaction mixture), the reaction will generally yield, in addition to a steroidal-21-aldehyde of formula IV, the corresponding steroidal-21-acetal formed with the alcohol solvent ($R_1$—OH); i.e., a steroid having the formula

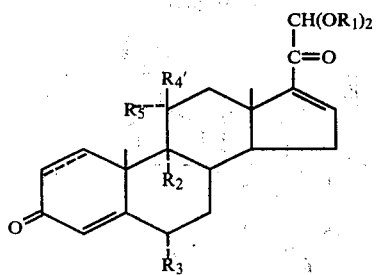

V

The oxidation reaction will generally be completed within a relatively short period of time, i.e., about 1 hour.

If the above described reaction is allowed to proceed for an extended period of time, e.g., more than about 24 hours, the major product will by the 20-hydroxy-21-carboxylic acid ester having the formula

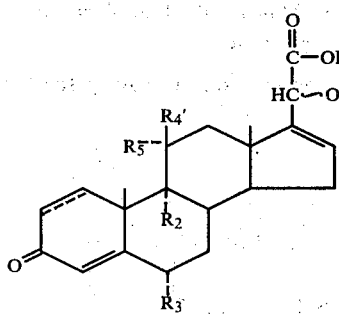

VI

If water is present as a co-solvent in the oxidation reaction, and the reaction is allowed to proceed for an extended period of time, in addition to the 20-hydroxy-21-carboxylic acid ester of formula VI, the corresponding 20-hydroxy-21-carboxylic acid will be produced; i.e., a steroid having the formula

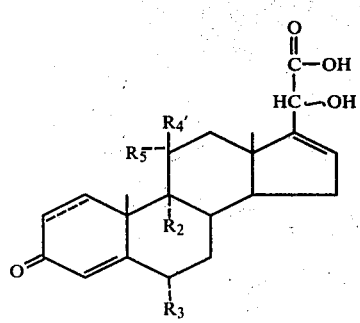

VII

The steroids of formulas VI and VII exist as mixtures of the 20α- and 20β-hydroxy-steroids.

Reaction of a mixture of a steroidal-21-aldehyde of formula IV and the corresponding steroidal-21-acetal of formula V with a mixture of (i) an inorganic cyanide catalyst (e.g., an alkali metal cyanide such as potassium cyanide); (ii) an oxidizing agent, e.g., a heavy metal oxide such as activated manganese dioxide or lead dioxide; (iii) an inert solvent, e.g., a halogenated hydrocarbon solvent such as dichloromethane or chloroform; (iv) a primary or secondary alcohol, $R_1'$-OH (throughout the specification $R_1'$ is any nontertiary $R_1$ group); and (v) an acid, e.g., acetic acid, which serves to neutralize the alkali cyanide catalyst; yields a steroid having the formula

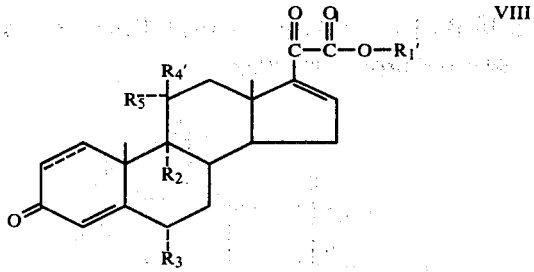

VIII

The 20α-and 20β-hydroxysteroids of formulas VI and VII can be oxidized to obtain the corresponding 20-ketosteroids, having the respective formulas

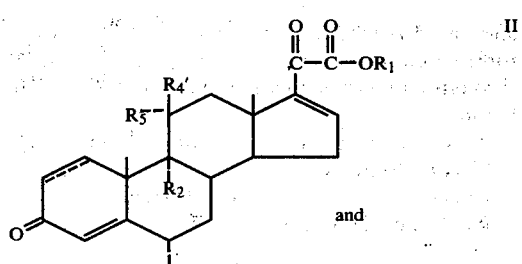

II and

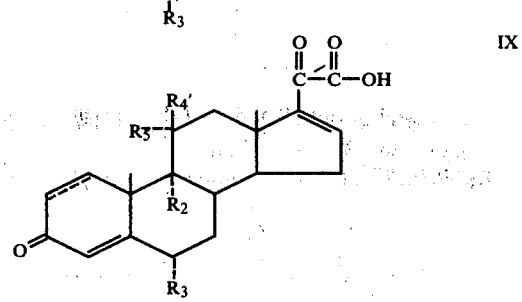

IX

Exemplary of suitable oxidizing agents are manganese dioxide and chromium dioxide. In the instance wherein the 20α-and 20β-hydroxy-steroids being oxidized have an 11β-hydroxy substituent, the steroids of formulas II and IX will be mixtures of 11β-hydroxy and 11-keto steroids.

The starting materials of formula II can also be prepared by esterification of the corresponding steroidal-21-oic acid of formula IX. (A steroid of formula IX can be prepared as described above, or alternatively, by saponification of a corresponding steroidal-21-oic acid ester of formula II or VIII).

The starting steroids of formula IIa can be prepared by esterification of the corresponding 11β-hydroxy-$\Delta^{4,16}$-pregnene of formula II with the appropriate carboxylic acid anhydride having the formula (R$_8$CO)$_2$O    (X).

The reaction proceeds in the presence of an organic base such as pyridine with heating.

Still another route for the preparation of the starting materials of formula II or IIa wherein $R_1$ is a non-tertiary group is the transesterification of another ester of formula VIII, II or IIa. The starting steroid is reacted with the appropriate alcohol in the presence of a basic alkoxide (e.g., sodium ethoxide or aluminum isopropoxide) or, preferably, a source of cyanide ion (e.g., an alkali metal cyanide such as sodium cyanide or potassium cyanide to yield the transesterification product.

16,17-Cis-diol functionality can be introduced into a $\Delta^{4,16}$-steroidal-21-carboxylic acid or derivative of formula II or IIa using any one of the many procedures well known in the art of organic chemistry. The following is a list of exemplary oxidation procedures:

(i) oxidation of a steroid of formula II or IIa with potassium permanganate (ii) oxidation of a steroid of formula II or IIa with osmium tetroxide followed by treatment with hydrogen sulfide;

(iii) oxidation of a steroid of formula II or IIa with a catalytic amount of osmium tetroxide in the presence of a molar equivalent of a tertiary amine oxide;

(iv) oxidation of a steroid of formula II or IIa with triphenylmethyl phosphonium permanganate;

(v) oxidation of a steroid of formula II or IIa with a mixture of acetic acid, iodine and potassium iodate followed by treatment with potassium acetate and sodium hydroxide;

(vi) oxidation of a steroid of formula II or IIa with a mixture of iodine and silver acetate followed by treatment with potassium hydroxide;

(vii) oxidation of a steroid of formula II or IIa with a mixture of thallium (III) acetate and acetic acid followed by treatment with potassium hydroxide; and (viii) oxidation of a steroid of formula II or IIa with 0.2 to 5% osmium tetroxide in the presence of tetraethyl ammonium acetate and t-butyl hydroperoxide.

The resulting steroid has the formula

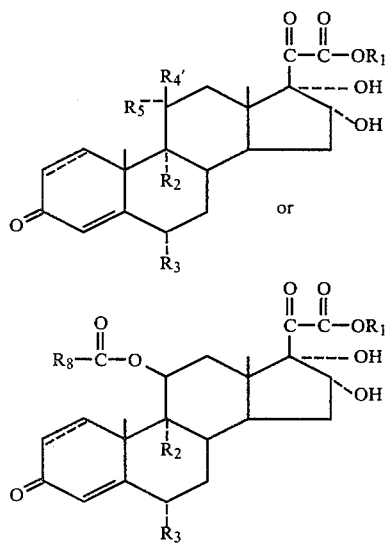

Those products of formula I wherein $R_6$ is hydrogen and $R_7$ is acyl can be prepared by acylation of the corresponding 16,17-cis-diol of formula XI or XIa with a carboxylic acid anhydride having the formula $(R_7'CO)_2O$   (XII)

in the presence of an organic base such as pyridine. In formula XII, $R_7'$ is alkyl, aryl or arylalkyl.

Those products of formula I wherein $R_6$ is acyl and $R_7$ is hydrogen can be prepared in a two step process from the corresponding 16,17-cis-diol of formula XI or XIa. Reaction of a 16,17-cis-diol of formula XI or XIa with a trialkyl-orthoester of the formula $R_9C(Oalkyl)_3$   (XIII)

in the presence of p-toluenesulfonic acid yields the corresponding intermediate having the formula

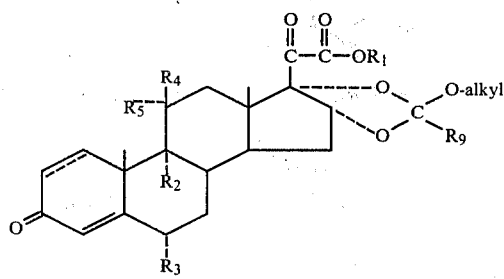

In formulas XIII and XIV and throughout the specification $R_9$ is alkyl, aryl, or arylalkyl. An intermediate of formula XIV can be treated with methanol, sodium acetate and acetic acid to yield the corresponding steroid product having the formula

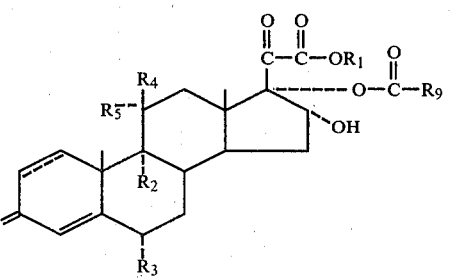

Those steroids of formula I which contain the same acyloxy group in the $11\beta,16\alpha$ and 17-positions can be prepared by reacting the appropriate 16,17-cis-diol of formula XI with a carboxylic acid anhydride in the presence of p-toluenesulfonic acid.

Those steroids of formula I wherein $R_6$ and $R_7$ are both acyl (either the same of different) can be prepared by reacting a steroid of formula XV with a carboxylic acid anhydride of formula XII in the presence of an organic base such as pyridine.

Still another route for the preparation of a steroid product of this invention wherein $R_1$ is a non-tertiary group is the transesterification of another product of this invention. The methodology is the same as that described above for the transesterification of a starting steroid of formula II, IIa or VIII.

The steroids produced by the process of this invention are physiologically active substances that possess glucocorticoid and anti-inflammatory activity. They can be used topically in the treatment of skin conditions such as dermatitis, sunburn, neurodermatitis, eczema, and anogenital pruritus. The compounds obtained by the process of this invention may be used in the range of 0.01 to 5.0% by weight, preferably 0.05 to 2.0% by weight in a conventional cream or lotion.

Preferred steroids of this invention are those having an $11\beta$-hydroxy group and most preferred are those having the structural formula

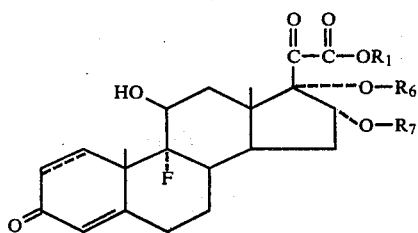

XVI

The following examples are specific embodiments of this invention.

EXAMPLE 1

(11β,16α)-9-Fluoro-11,16,17-trihydroxy-3,20-dioxo-pregna-1,4-dien-21-oic acid, methyl ester To cooled and stirred acetone (75 ml, reagent grade) at 0° C. the following two solutions were added simultaneously at the same rate in the period of 15 minutes:

(1) A solution of 1.16 g of (11β)-9-fluoro-11-hydroxy-3,20-dioxopregna-1,4,16-trien-21-oic acid, methyl ester in acetone (110 ml) reagent grade) containing 37% formic acid (4 ml); and (2) A solution of 711 mg of potassium permanganate in a mixture of acetone (97 ml, reagent grade) and water (10 ml).

After the addition is complete the mixture is stirred for 0.5 hour at 0° C. The excess potassium permanganate is quenched with a few drops of 30% hydrogen peroxide and the mixture is warmed to 40° C. and filtered through a bed of HYFLO. The filtrate is evaporated in vacuo to give a gummy material which is dissolved in chloroform and chromatographed on a 25 g-silica gel column. Elution with ethyl acetate-chloroform (1:9, 1:4 and 1:1) gives 785 mg of an impure title compound. This is rinsed with warm chloroform and filtered. The solid (500 mg) is recrystallized from chloroform-methanol to give 380 mg (30%) of a tlc-homogenous and analytical specimen of the title compound, melting point 306°–308° C., with consistent spectra data.

Anal. Calc'd for $C_{22}H_{27}FO_7$: C,62.55; H,6.44; F,4.50. Found: C,62.47; H,6.65; F,4.43.

EXAMPLE 2

(11β,11α)-16-(Acetyloxy)-9-fluoro-11,17-dihydroxy-3,20-dioxopregna-1,4-dien-21-oic acid, methyl ester A solution of 650 mg of (11β,16α)-9-fluoro-11,16,17-trihydroxy-3,20-dioxopregna-1,4-dien-21-oic acid, methyl ester (see Example 1) and 3 ml of acetic anhydride in 40 ml of pyridine is stirred at room temperature under a nitrogen atmosphere for 20 hours. The solvent is evaporated in vacuo at room temperature and the residue is diluted with chloroform. The chloroform solution is washed with 5% hydrochloric acid solution and water, dried over anhydrous $Na_2SO_4$ and evaporated in vacuo to give a foam. This is dissolved in chloroform-hexane (9:1) and chromatographed on a 30 g-silica gel column. Elution with ethyl acetate-chloroform (1:9) gives 570 mg of a slightly impure title compound. Crystallization from acetone-hexane gives 450 mg of a tlc-homogeneous and analytical specimen, melting point 244°–245° C. (dec.), with consistent spectra data.

Anal. calc'd for $C_{24}H_{29}FO_8$: C,62.06; H,6.29; F,4.09. Found: C,61.98; H,6.21; F,4.00.

EXAMPLE 3

(11β,16α)-9-Fluoro-11,16,17-trihydroxy-3,20-dioxo-pregna-1,4-dien-21-oic acid, 2-methylethyl ester A solution of (11β,16α)-9-fluoro-11,16,17-trihydroxy-3,20-dioxopregna-1,4-dien-21-oic acid, methyl ester (1.0 g) in anhydrous isopropyl alcohol (100 ml) containing sodium cyanide (100 mg) is refluxed for 3.0 hours. The isopropanol is then removed by distillation in vacuo and the residue is washed with water, dried and crystallized to afford the title compound.

EXAMPLE 4

11β,16α,17-Triacetyloxy-9-fluoro-3,20-dioxopregna-1,4-dien-21-oic acid, methyl ester A suspension of (11β,16α)-9-fluoro-11,16,17-trihydroxy-3,20-dioxopregna-1,4-dien-21-oic acid, methyl ester (150 mg) in a mixture of glacial acetic acid (5.0 ml) and acetic anhydride (5.0 ml) containing p-toluene sulfonic acid hydrate (150 mg) is stirred for 40 hours. Sodium acetate (300 mg) is added and the solution is evaporated in vacuo. The residue is diluted with water, extracted with chloroform and the chloroform extract is washed with water, dried ($MgSO_4$) and evaporated to a solid. The solid is crystallized from ethyl acetate to afford the title compound (164 mg), melting point 317°–319° C. (dec.) (discoloration starts from ca. 280° C.).

EXAMPLE 5

(11β,16α)-17-(Acetyloxy)-9-fluoro-11,16-dihydroxy-3,20-dioxopregna-1,4-dien-21-oic acid, methyl ester (A) 2'-Ethoxy-9-fluoro-11β-hydroxy-2'-methyl-3,20-dioxopregna-1,4-dieno-[16α,17d]-1,3-dioxolane-21-oic acid, methyl ester A solution of (11β,16α)-9-fluoro-11,16,17-trihydroxy-3,20-dioxopregna-1,4-dien-21-oic acid, methyl ester (1.0 g) in dry dimethylformamide (30 ml) containing triethyl ortho acetate (3.0 ml) and p-toluene sulfonic acid hydrate (30 mg) is heated in a bath at 130° C. for 5–6 hours. Pyridine (0.2 ml) is added and the mixture is poured into water and extracted with chloroform. The chloroform extract is washed with water, dried ($MgSO_4$) and evaporated to afford the title compound.

(B) (11β,16α)-17-(Acetyloxy)-9-fluoro-11,16-dihydroxy-3,20-dioxopregna-1,4-dien-21-oic acid, methyl ester A solution of 2'-ethoxy-9-fluoro-11β-hydroxy-2'-methyl-3,20-dioxopregna-1,4-dieno-[16α,17-d]-1,3-dioxolane-21-oic acid, methyl ester (1.0 g) in methanol (30 ml) containing 0.1 N sodium acetate (0.3 ml) and 0.1 N acetic acid (2.5 ml) is refluxed for several hours until the starting steroid disappears as shown by thin layer chromatography. The methanol is then evaporated in vacuo and the residue is washed with water, and dried. It is then dissolved in chloroform and chromatographed over a column of silica gel to afford the title compound.

EXAMPLE 6

(16α,17)-Bis acetyloxy-9-fluoro-11β-hydroxy-3,20-dioxopregna-1,4-dien-21-oic acid, methyl ester A solution of (11β,16α)-17-acetyloxy-9-fluoro-11,16-dihydroxy-3,20-dioxopregna-1,4-dien-21-oic acid, methyl ester (1.0 g) is acetylated with acetic anhydride in pyridine for 3.0 hours. The solution is poured into an excess of 20% hydrochloric acid and is extracted with chloroform. The chloroform solution is washed with a dilute sodium bicarbonate solution and water, dried (MgSO$_4$) and evaporated to afford the title compound.

What is claimed is:

1. A steroid having the formula

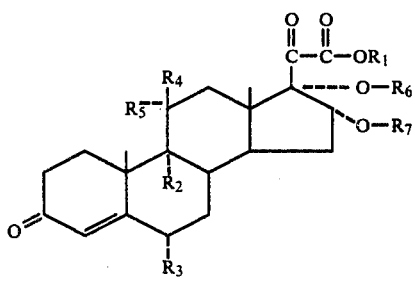

or the 1,2-dehydro derivative thereof, wherein
$R_1$ is alkyl of 1 to 10 carbon atoms, aryl, or arylalkyl;
$R_2$ is hydrogen or halogen;
$R_3$ is hydrogen, fluorine or methyl;
$R_4$ is chlorine, fluorine, hydroxy or

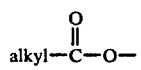

and $R_5$ is hydrogen, or $R_4$ and $R_5$ together are =O; and
$R_6$ and $R_7$ each is independently hydrogen,

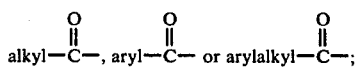

wherein the terms "alkyl" and "alkoxy" refer to groups having 1 to 6 carbon atoms and the term "aryl" refers to phenyl or phenyl substituted with one or more halogen, alkyl and alkoxy groups.

2. A steroid in accordance with claim 1 wherein $R_6$ and $R_7$ each is hydrogen.

3. A steroid in accordance with claim 1 wherein $R_6$ is hydrogen and $R_7$ is

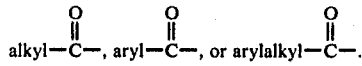

4. A steroid in accordance with claim 1 wherein $R_6$ is

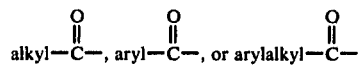

and $R_7$ is hydrogen.

5. A steroid in accordance with claim 1 having the formula

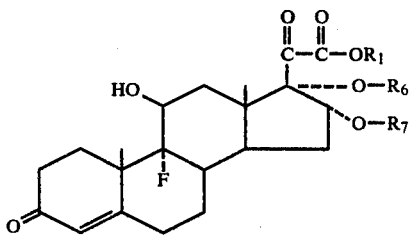

or the 1,2-dehydro derivatives thereof.

6. A steroid in accordance with claim 5 wherein $R_6$ and $R_7$ each is hydrogen.

7. A steroid in accordance with claim 5 wherein $R_6$ is hydrogen and $R_7$ is

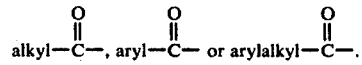

8. The compound in accordance with claim 1 (11β,16α)-9-fluoro-11,16,17-trihydroxy-3,20-dioxo-pregna-1,4-dien-21-oic acid, methyl ester.

9. The compound in accordance with claim 1 (11β,16α)-16-(acetyloxy)-9-fluoro-11,17-dihydroxy-3,20-dioxopregna-1,4-dien-21-oic acid, methyl ester.

* * * * *